United States Patent [19]

Beatty et al.

[11] Patent Number: 5,659,916
[45] Date of Patent: Aug. 26, 1997

[54] LOTION APPLICATOR

[76] Inventors: Georgia Beatty; T. Stephen Beatty, both of P.O. Box 1648, Huntersville, N.C. 28078

[21] Appl. No.: 449,942

[22] Filed: May 25, 1995

[51] Int. Cl.$^6$ ................................ B05C 1/06; A47K 7/03
[52] U.S. Cl. ...................... 15/210.1; 15/209.1; 15/143.1; 15/144.1; 15/244.2; 81/489; 401/262; D4/129; D8/313; 16/110 R
[58] Field of Search ................ 15/143.1, 144.1, 15/211, 210.1, 209.1, 229.13, 244.2, 244.3, 229.6, 145; 81/489; 16/110 R, 114 R, 125, 112; D4/129, 131; 401/261, 262, 88, 98; D8/313; 7/167, 168

[56] References Cited

U.S. PATENT DOCUMENTS

| | | | |
|---|---|---|---|
| D. 246,804 | 12/1977 | Kaslan | D28/7 |
| D. 289,564 | 4/1987 | Harford | D28/7 |
| D. 307,490 | 4/1990 | Thierott, Jr. et al. | D28/7 |
| D. 310,270 | 8/1990 | Bacal et al. | D28/7 |
| D. 360,989 | 8/1995 | Laubach, III et al. | D4/129 |
| 1,579,463 | 4/1926 | Winters | 15/143.1 |
| 1,592,882 | 7/1926 | Artas | 15/143.1 |
| 1,790,466 | 1/1931 | Gordon | 15/143.1 |
| 2,127,674 | 8/1938 | Clarke | 15/143.1 |
| 2,625,702 | 1/1953 | Grubbs | 15/144.1 |
| 2,653,335 | 9/1953 | Johnson | 15/145 |
| 3,204,277 | 9/1965 | Vismer et al. | 15/211 |
| 3,870,419 | 3/1975 | Sage | 401/8 |
| 4,236,270 | 12/1980 | Mavis | 15/144.1 |
| 4,299,005 | 11/1981 | Brown | 15/244.2 |
| 4,381,766 | 5/1983 | Avolio | 128/62 R |
| 4,654,921 | 4/1987 | Dinner | 15/143.1 |
| 4,765,766 | 8/1988 | Heitmann et al. | 401/48 |
| 5,240,339 | 8/1993 | DeForest et al. | 401/207 |

FOREIGN PATENT DOCUMENTS

| | | | |
|---|---|---|---|
| 292523 | 12/1935 | Italy | 15/143.1 |

*Primary Examiner*—Gary K. Graham
*Attorney, Agent, or Firm*—John D. Gugliotta; David Z. Volk

[57] ABSTRACT

An improved handle relating generally to applicators for applying body lotions is provided, wherein the handle may be easily held and retained by a user with limited gripping strength or limited gripping ability due to arthritis and other physically challenging limitations, for instance. A preferred embodiment of the improved handle comprises a curved elongated shaft having a gripping portion integral to one end and a pivotal mounting portion for mounting an applicator pad to an opposing end. The gripping portion defines an orifice, preferably D-shaped, through which fingers or a thumb of a hand may be inserted for damping of the gripping portion between the fingers and the thumb. The gripping portion provides multiple subshafts separated by integral sidewalls. Retaining stability is provided according to the position that the user desires to maneuver the elongated shaft by cooperatively integrating the fingers, the thumb, and a wrist portion of the hand around, within, against, or about the multiple subshafts, thereby to enhance retention of the gripping portion, and thus the handle, by the hand having limited gripping ability.

3 Claims, 4 Drawing Sheets

LOTION APPLICATOR

BACKGROUND OF THE INVENTION

1. Field of the Invention

The present invention relates generally to applicators for applying body lotions, such as moisturizing lotions, skin care lotions and sunscreens, onto the back and other parts of the body that are ordinarily difficult to reach and, more particularly, to an improved handle for such applicators, which handle may be easily held and retained by a user with limited gripping strength or limited gripping ability due to arthritis and other physically challenging limitations.

2. Description of the Related Art

As is well-known in the art, moisturizing lotions, skin care lotions and sunscreens must typically be applied regularly, uniformly and consistently over large skin areas of the body to achieve optimum effectiveness. Most individuals find it difficult or impossible to apply such body lotions to their backs unassisted. Many individuals also have difficulty applying such lotions to their lower legs or other areas which may be hard to reach due to chronic back problems, arthritic joint conditions and the like. Those areas of the body that require twisting, reaching or bending to access such areas can cause considerable difficulty for individuals afflicted with such conditions, particularly when required on a daily or more frequent repetitive basis.

Numerous attempts have been made to correct for the foregoing problems. For instance, U.S. Pat. No. 5,240,339, issued in the name of DeForest et al., discloses a body lotion applicator with an extended applicator head for reaching the back and other portions of the body that are difficult to reach. Further, U.S. Pat. No. 4,381,766, issued in the name of Avolio, discloses a back applicator with a hinged and curved handle with a free-floating applicator pad mounted thereupon, for applying lotions, creams, oils, and other medicating substances to the back area where it is difficult to reach. Similarly, ornamental designs for suntan lotion applicators are disclosed in U.S. Pat. No. Des. 310,270, issued in the name of Bacal et al., and in U.S. Pat. No. Des. 307,490, issued in the name of Thieroff, Jr. et al. However, applicators made in accordance with these references are associated with several drawbacks. In particular, the elongated handle of the related art must be gripped with sufficient strength to retain the handle within the hand gripping the handle. As such, handles of the related art present gripping problems for a user with limited gripping strength or limited gripping ability due to arthritis and other physically challenging limitations. The handles of the related art cannot be sufficiently gripped and retained by users with such limitations; as a result, the handle cannot be picked up or otherwise falls from the hand of a user who attempts to use the associated applicator without having sufficient gripping strength or gripping ability to retain the handle.

Consequently, a need has been felt for providing an improved handle for body lotion applicators, wherein the handle overcomes the gripping problems experienced by a user with limited gripping strength or limited gripping ability due to arthritis and other physically challenging limitations.

SUMMARY OF THE INVENTION

It is therefore an object of the present invention to provide an improved handle for body lotion applicators, wherein the handle may be retained by a user with limited gripping strength or limited gripping ability.

It is another object of the present invention to provide an improved handle that may be retained with minimal gripping effort.

It is a feature of the present invention to provide an improved handle that has an open gripping portion, preferably D-shaped, through which a user's hand may be slipped in a variety of positions, wherein the hand is retained within the open gripping portion with minimal gripping effort provided by the hand.

Briefly described according to one embodiment of the present invention, an improved handle relating generally to applicators for applying body lotions is provided, wherein the handle may be easily held and retained by a user with limited gripping strength or limited gripping ability due to arthritis and other physically challenging limitations, for instance. A preferred embodiment of the improved handle comprises a curved elongated shaft having a gripping portion integral to one end and a pivotal mounting portion for mounting an applicator pad to an opposing end. The gripping portion defines an orifice, preferably D-shaped, through which fingers or a thumb of a hand may be inserted for clamping of the gripping portion between the fingers and the thumb. The gripping portion provides multiple subshafts separated by integral sidewalls. Retaining stability is provided according to the position that the user desires to maneuver the elongated shaft by cooperatively integrating the fingers, the thumb, and a wrist portion of the hand around, within, against, or about the multiple subshafts, thereby to enhance retention of the gripping portion, and thus the handle, by the hand having limited gripping ability.

In accordance with a preferred embodiment, in a handle that is grippable and retainable by a user with limited gripping ability due to arthritus and other physically challenging limitations, wherein the handle is used for an applicator of body lotions to portions of the body that are difficult to reach, the improvement comprising: a curved elongated shaft with a gripping portion integrally molded thereto at a first end of the shaft, wherein the gripping portion comprises a first and second subshaft extending longitudinally from the shaft and separated by opposing first and second integral sidewalls, thereby to define an orifice into which fingers of a hand cupping the first subshaft may be received, in order to provide a surface of leverage with the second subshaft against which a wrist portion of the hand cupping the first subshaft may press to stabilize the first subshaft within the hand, thereby to provide increased grip and retention of the handle by the hand cupping the first subshaft with a limited grip.

An advantage of the present invention is that the handle is easy to retain while applying body lotions to areas of the body that are difficult to reach.

Another advantage of the present invention is that a user with limited gripping ability due to arthritis and other physical limitations may easily retain the handle with minimal gripping effort.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
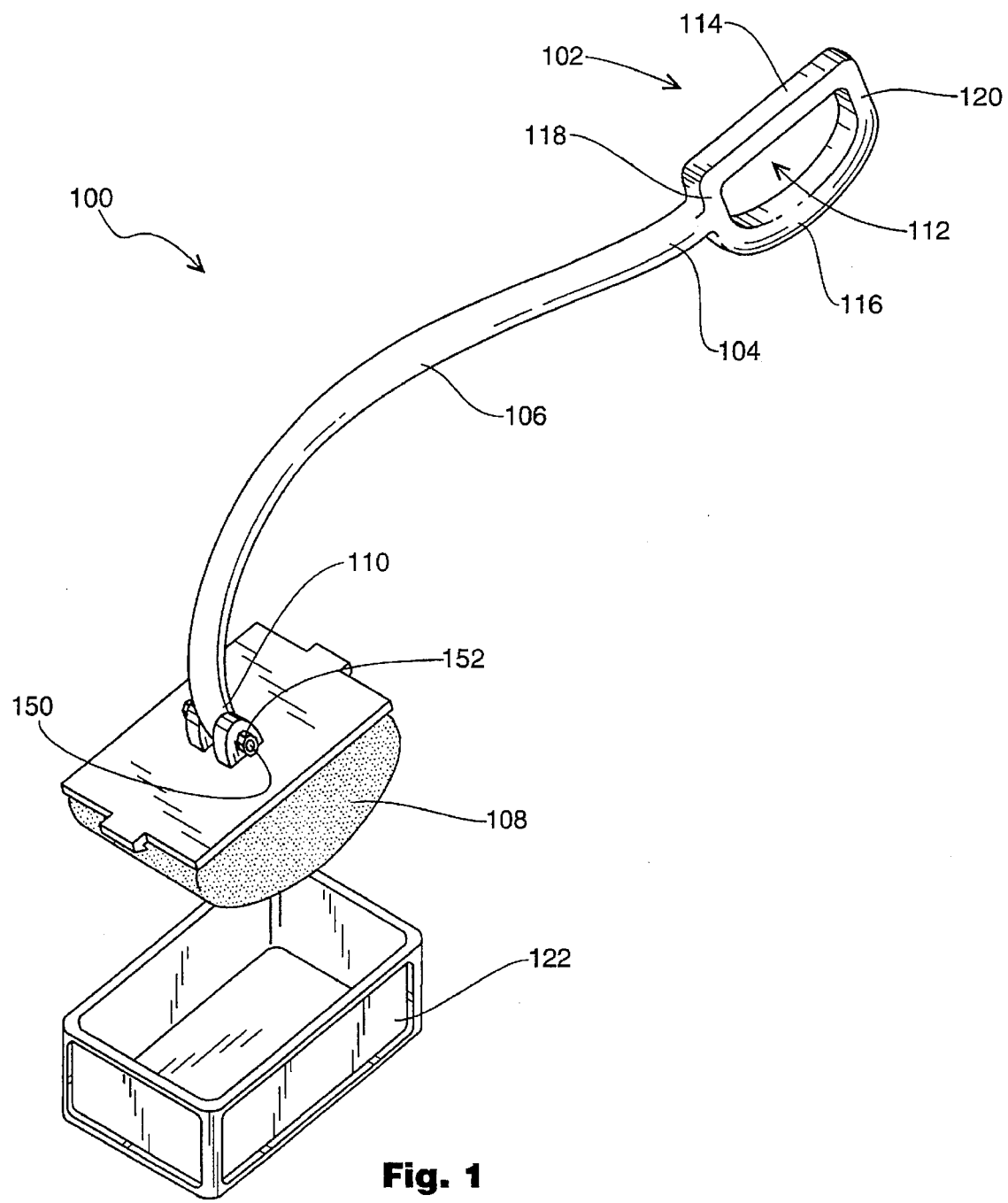
FIG. 1 is a top and side perspective view of an elongated and curved handle with an open gripping portion according to a preferred embodiment of the present invention, showing an applicator pad pivotally attached thereto and an associated storage tray for the applicator pad.

Referring now to FIG. 1, an improved handle 100 is shown, according to a preferred embodiment of the present invention, to be used by a user (not shown) with limited gripping ability for applying body lotions to parts of the body that are difficult to reach. A gripping portion 102 is preferably integrally molded or otherwise attached to a first end 104 of an elongated shaft 106. A conventional applicator pad 108 is removably pivotally mounted to a second end 110 of the shaft 106 in a manner well-known in the art, thereby to provide pivotal motion of the pad 108 with respect to the shaft 106. A preferred embodiment of the present invention removably pivotally mounts the conventional applicator pad 108 with a bolt 150 inserted through the second end 110 of the shaft 106 and secured with a threaded nut 152. Another preferred embodiment of the present invention removably mounts the applicator pad 108 with conventional hook-and-loop fastener material (not shown), commonly having a brandname of Velcro®, for instance.

A preferred embodiment of the elongated shaft 106 is arched or otherwise curved, thereby to provide room for the user to maneuver the shaft 106 across her back. A preferred embodiment of the gripping portion 102 defines an orifice 112, preferably D-shaped, with a first subshaft 114 and an opposing second subshaft 116, which subshafts extend longitudinally from the shaft 106 and are separated by opposing first and second sidewalls 118 and 120, wherein the first sidewall 118 is integral with the shaft 106 and the first and second subshafts 114 and 116 are integral with the first sidewall 118 as well as with the opposing sidewall 120, thereby to define the orifice 112. Also shown in FIG. 1 is a storage tray 122, which tray is shaped to house the applicator pad 108 when not in use. A preferred embodiment of the storage tray 122 attaches to the pivotally mounted applicator pad 108 in a conventional manner, thereby to provide a single unit of the applicator pad 108 and the storage tray.

2. Operation of the Preferred Embodiment

Figure 2:
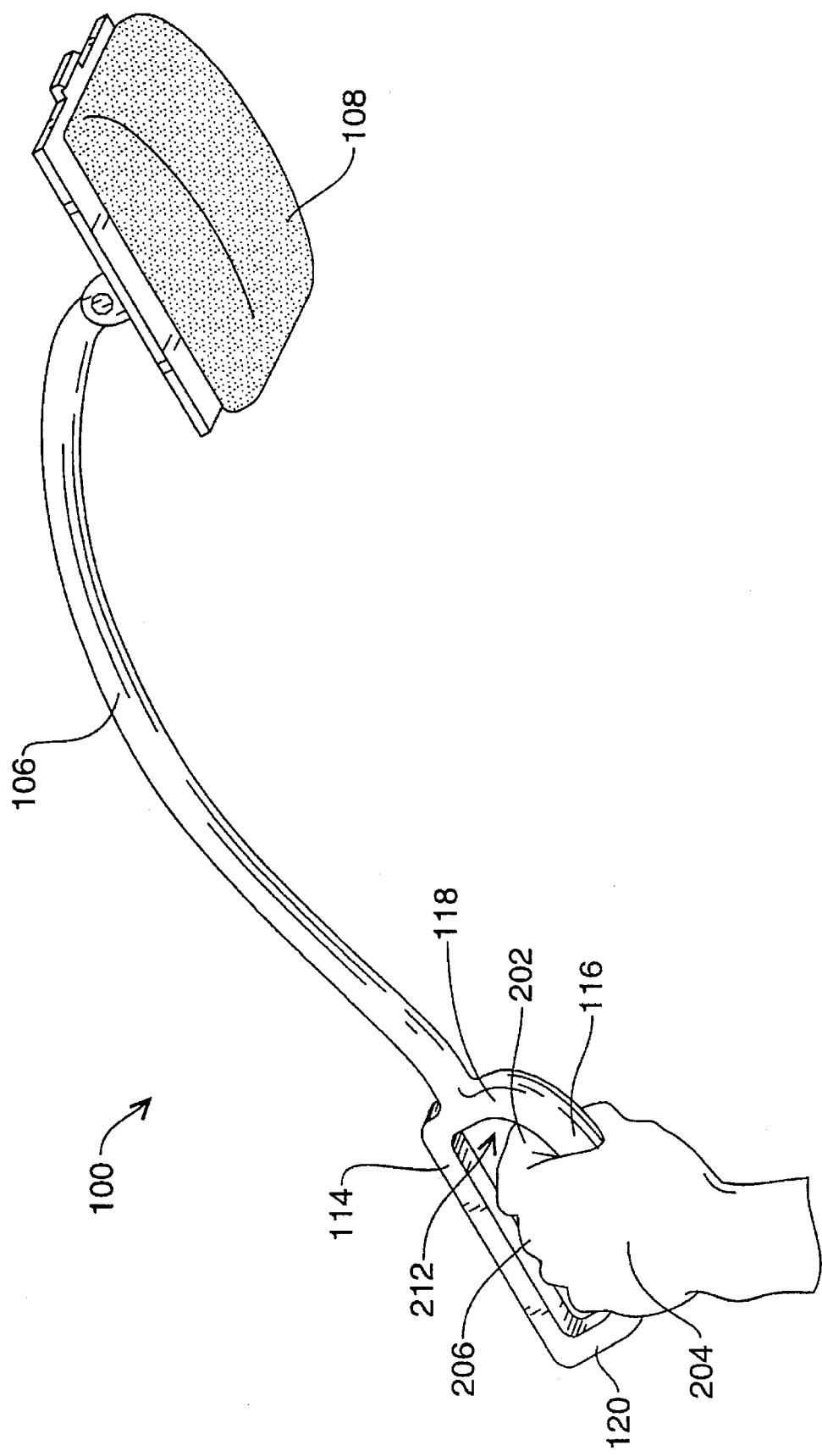
FIG. 2 is a bottom and side perspective view of the handle of the present invention being gripped at the open gripping portion by a hand in a first position.
Figure 3:
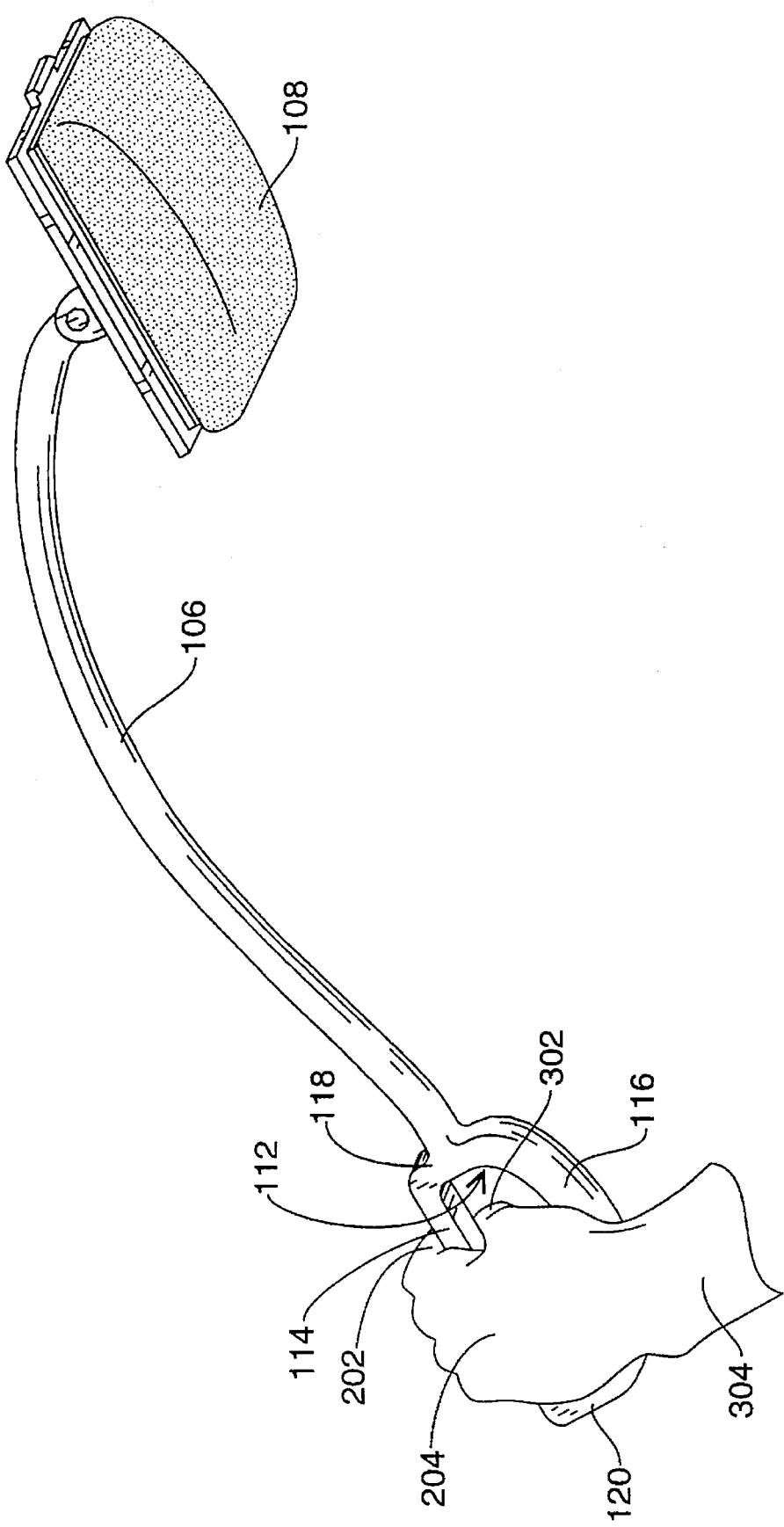
FIG. 3 is a bottom and side perspective view of the handle of the present invention being gripped at the open gripping portion by a hand in a second position.
Figure 4:
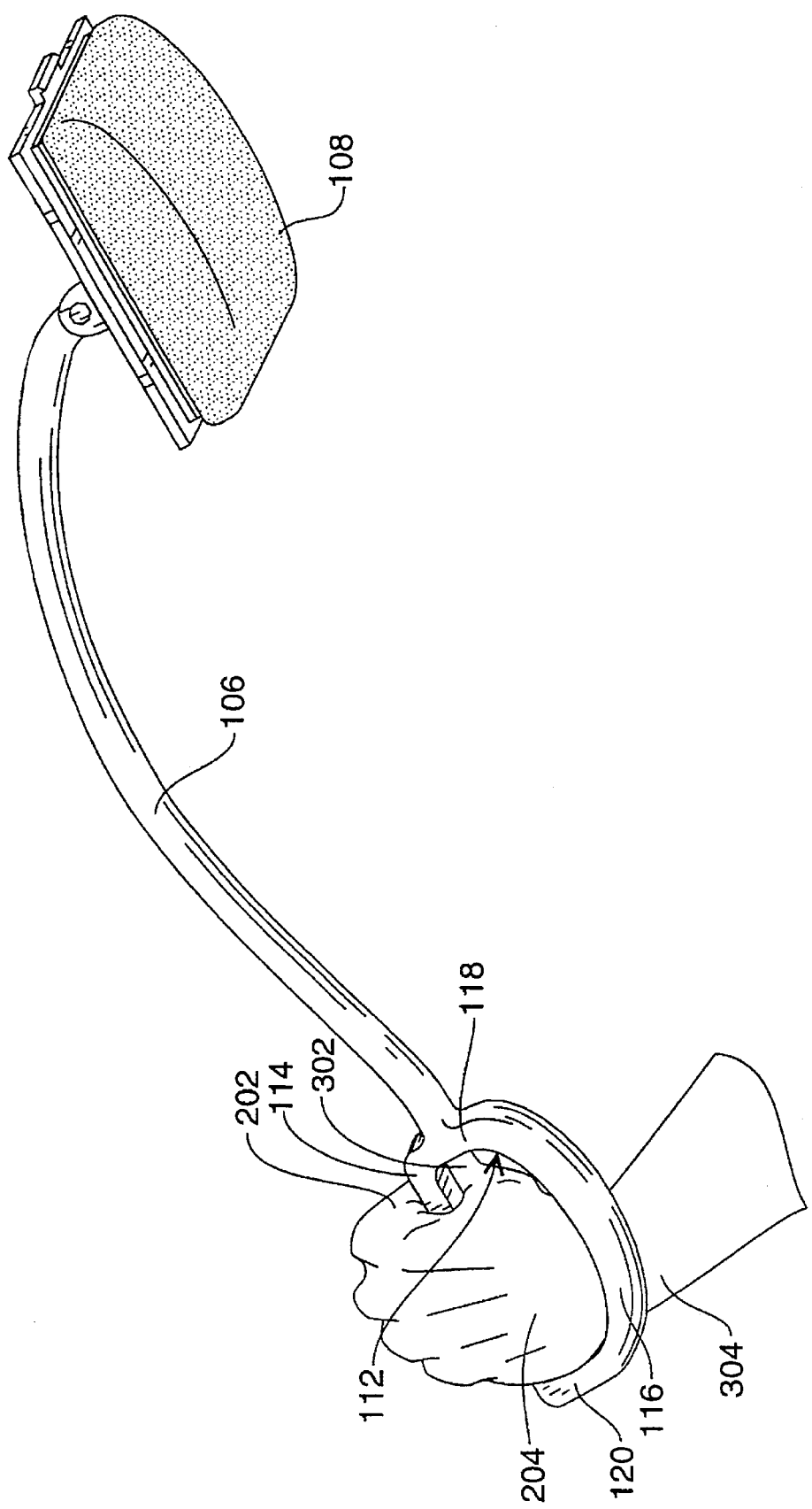
FIG. 4 is a bottom and side perspective view of the handle of the present invention being gripped at the open gripping portion by a hand in a third position.

In operation, as shown in FIGS. 2, 3, and 4, the present invention may be gripped in a plurality of gripping positions, according to the amount of gripping ability available to the user from the user's hand, and according to the position in which the user desires to place the elongated shaft 106 and the pivotally mounted applicator pad 108. FIG. 2 shows a preferred gripping position to be used by a user with sufficient gripping ability to retain the handle 100 without additional support from the first subshaft 114 of the handle. In FIG. 2, a user inserts her fingers 202 of her hand 204 through the orifice 112, thereby to cup the fingers 202 in a gripping manner about the second subshaft 116, thereby to retain the handle 100. The first subshaft 114 is preferably positioned above the user's knuckles 206, thus out of the way. The opposing sidewalls 118 and 120 prevent the hand 204 from slipping off of the second subshaft 116 and toward or away from the shaft 106, thereby to retain the the fingers 202 within the orifice 112 when the handle is being maneuvered by the hand 204, such as across the user's back (not shown), for instance.

In FIG. 3, a user with limited gripping ability due to arthritis and other physically challenging limitations, for instance, inserts her thumb 302 of her hand 204 through the orifice 112, thereby to mildly clamp the first subshaft 114 between the fingers 202 and the thumb 302, thereby to retain the handle 100. The second subshaft 116 is preferably positioned below the user's thumb 302 and against the user's wrist portion 304, thereby to provide retaining stability against the wrist portion 304 when the first subshaft 114 is mildly clamped between the thumb 302 and the fingers 202. The opposing sidewalls 118 and 120 prevent the mildly clamped thumb 302 from slipping off of the first subshaft 114 and toward or away from the shaft 106, thereby to retain the thumb 302 within the orifice 112 when the handle is being maneuvered by the hand 204, such as across the user's back (not shown), for instance.

Similarly, in FIG. 4, a user with limited gripping ability due to arthritis and other physically challenging limitations, for instance, inserts her fingers 202 of her hand 204 through the orifice 112, thereby to cup the fingers 202 in a gripping manner about the first subshaft 114 and to mildly clamp the first subshaft 114 between the fingers 202 and the thumb 302, thereby to retain the handle 100. The second subshaft 116 is preferably positioned below the user's thumb 302, against and atop the user's wrist portion 304, thereby to provide retaining stability against the wrist portion 304 when the first subshaft 114 is mildly clamped between the fingers 202 and the thumb 302. The opposing sidewalls 118 and 120 prevent the mildly clamped fingers 202 from slipping off of the subshaft 116 and toward or away from the shaft 106, thereby to retain the thumb 302 within the orifice 112 when the handle is being maneuvered by the hand 204, such as across the user's back (not shown), for instance.

Thus, there has been shown and described an improved handle relating generally to applicators for applying body lotions, which handle may be easily held and retained by a user with limited gripping strength or limited gripping ability due to arthritis and other physically challenging limitations, for instance, and which handle fulfills all the objects and advantages sought therefore. Many changes, modifications, variations and other uses and applications of the subject invention will, however, become apparent to those skilled in the art after considering this specification and the accompanying drawings which disclose a preferred embodiment thereof. All such changes, modifications, variations and other uses and applications which do not depart from the spirit and scope of the invention are deemed to be covered by the invention which is limited only by the claims which follow.

What is claimed is:

1. A lotion applicator comprising:
   a. an elongated shaft having a shaft first end and a shaft second end;
   b. an application pad mounted to the shaft second end;
   c. a D-shaped gripping portion connected to the shaft first end, the gripping portion extending outwardly from the shaft first end in a direction away from the application pad;
   d. the gripping portion comprising a substantially straight elongated first member adapted to be grasped by a human hand and having a first end and a second end;
   e. the gripping portion further comprising an elongated, substantially straight first leg having a first leg first end and a first leg second end, the first leg first end connected to the first end of the first member, the first leg forming a substantially perpendicular angle with the first member and, the elongated shaft coupled to said first leg intermediate said ends thereof;

f. the gripping portion further comprising an elongated, substantially straight second leg having a second leg first end and a second leg second end, the second leg first end connected to the second end of the first member, the second leg forming a substantially perpendicular angle with the first member;

g. the gripping portion further comprising a curved elongated second member extending from the first leg second end the second member coupled at opposite ends thereof to the second ends of the legs, to the second leg second end, the second member being devoid of finger grip depressions; and h. the first member, the second member, the first leg and the second leg defining an opening there-between, the opening sized to permit a palm of an average-sized adult hand to fit therein.

2. The lotion applicator of claim 1, wherein the shaft is curved.

3. The lotion applicator of claim 2, wherein the application pad is pivotally mounted to the second end of the shaft.

* * * * *